United States Patent
Hsieh

(10) Patent No.: US 11,850,094 B2
(45) Date of Patent: Dec. 26, 2023

(54) ULTRASONIC TRANSDUCER WITH ZIPPER ARRAY OF TRANSDUCING ELEMENTS

(71) Applicant: Cheng-Yuan Hsieh, Hsinchu (TW)

(72) Inventor: Cheng-Yuan Hsieh, Hsinchu (TW)

(*) Notice: Subject to any disclaimer, the term of this patent is extended or adjusted under 35 U.S.C. 154(b) by 4 days.

(21) Appl. No.: 17/666,920

(22) Filed: Feb. 8, 2022

(65) Prior Publication Data

US 2022/0249059 A1    Aug. 11, 2022

(30) Foreign Application Priority Data

Feb. 9, 2021   (TW) .................. 110105150

(51) Int. Cl.
| | |
|---|---|
| A61B 8/00 | (2006.01) |
| B06B 1/06 | (2006.01) |
| A61B 17/34 | (2006.01) |
| A61B 8/08 | (2006.01) |

(52) U.S. Cl.
CPC .......... A61B 8/4494 (2013.01); A61B 8/0841 (2013.01); B06B 1/0622 (2013.01); *A61B 2017/3413* (2013.01); *B06B 2201/76* (2013.01)

(58) Field of Classification Search
CPC ... A61B 8/4494; A61B 8/0841; A61B 8/4477; A61B 2017/3413; B06B 1/0622; B06B 1/0292; B06B 2201/76
See application file for complete search history.

(56) References Cited

U.S. PATENT DOCUMENTS

| | | | | |
|---|---|---|---|---|
| 5,583,303 | A * | 12/1996 | Franz | G06F 3/045 |
| | | | | 73/862.68 |
| 11,531,083 | B2 * | 12/2022 | Stokes | G01S 7/2813 |
| 2012/0184854 | A1 * | 7/2012 | Raju | A61B 8/4236 |
| | | | | 600/459 |
| 2016/0038119 | A1 * | 2/2016 | Desjardins | A61B 8/4444 |
| | | | | 600/424 |
| 2020/0196991 | A1 * | 6/2020 | Schmied | A61B 8/5246 |
| 2020/0249079 | A1 * | 8/2020 | Akkaraju | G01H 11/08 |

FOREIGN PATENT DOCUMENTS

JP    2015062453 A  *  4/2015

* cited by examiner

*Primary Examiner* — Boniface Ngathi
*Assistant Examiner* — Zainab Mohammed Aldarraji
(74) *Attorney, Agent, or Firm* — BACON & THOMAS, PLLC

(57) ABSTRACT

This invention provides an ultrasonic transducer with a zipper array of transducing elements, which includes a tail and a head. A surface of the head is embedded with a plurality of left transducing elements and a plurality of right transducing elements, wherein each left transducing element at least partially overlaps each right transducing element in an elevation axis.

17 Claims, 19 Drawing Sheets

(a) Needle in plane (b) Needle not in plane
Or needle partially in plane

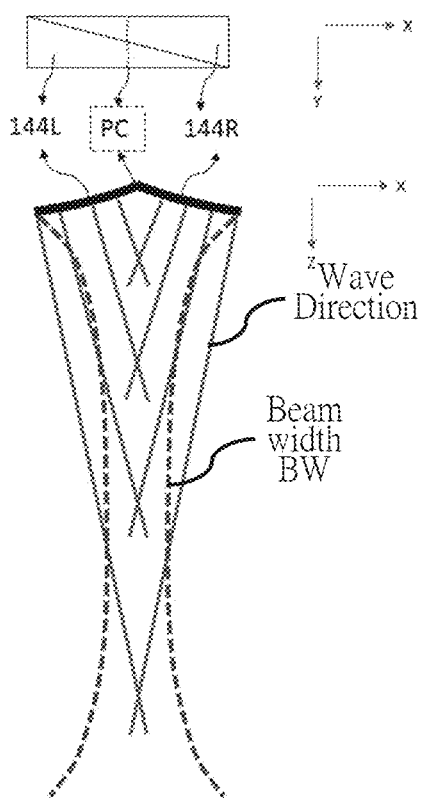
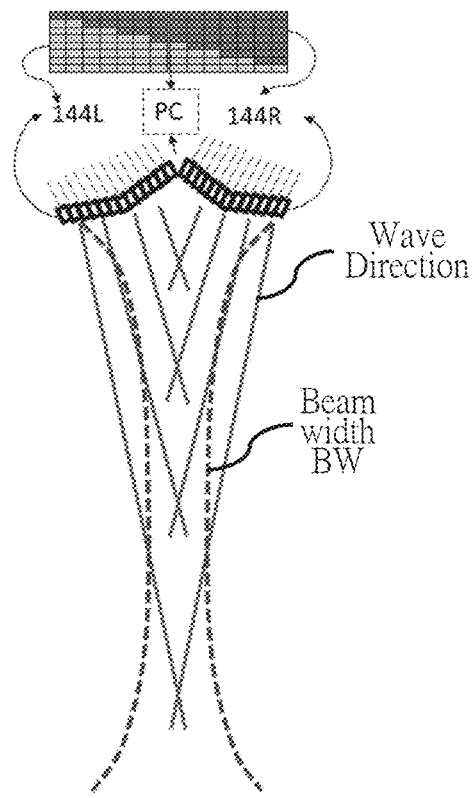
Folded convex zipper-grouped M-column-N-row micro array of transducing elements (folded convex ZMN)
FIG. 11E
FIG. 11F

ULTRASONIC TRANSDUCER WITH ZIPPER ARRAY OF TRANSDUCING ELEMENTS

CROSS REFERENCE TO RELATED APPLICATION

This application claims the benefits of the Taiwan Patent Application Serial Number 110105150, filed on Feb. 9, 2021, the subject matter of which is incorporated herein by reference.

BACKGROUND OF THE INVENTION

1. Field of the Invention

The present invention relates to an ultrasonic system with a zipper array of transducing elements, which improves needle visualization and intelligent stereotactic needle navigation.

2. Description of Related Art

When performing a medical operation or a body examination, a needle or a needle-like instrument may be inserted into a patient's body. To ensure a correct needle moving direction, an ultrasonic transducer is used to detect the position and the moving direction (or trajectory) of the needle.

FIGS. 1A and 1B show a needle navigation problem in the prior art, typically known as "needle not in plane" problem. One longitudinal plane (hereinafter, "1L") linear transducer 90 can detect an image plane 92. However, as shown in FIG. 1A, there is a high probability that the needle 94 not entirely but only partially intersects the image plane 92 because of unintended technical errors, making it difficult to precisely and safely control the position and the moving direction of the needle 94.

By observing image plane 92 in FIG. 1A, the user will only see the intersecting part of the needle 94 and do not know if other possible moving directions of the needle (including mirror directions) in FIG. 1B exist. Therefore, to further confirm that the needle 94 is completely "in plane" or to exclude possible moving directions of the needle which is out of the plane 92, the user may rotate the transducer clockwise, counterclockwise or even reinsert the needle. This process is unfavorable to an ultrasound guided needle injection, which requires great expertise after repeated training.

FIG. 1C shows a known solution to the problem of the needle "not in plane". An experienced user knows to tilt the transducer 90 to collect more tilted image planes 92, which helps confirm the moving direction of the needle 94. However, this kind of solution depends on the user's experience to reconstruct 3D information from multiple tilted nearby 2D image planes, so there is still a great probability to rotate the transducer to a wrong direction.

Therefore, it is desirable to provide an improved ultrasonic system, to obviate or mitigate the aforementioned problem.

SUMMARY OF THE INVENTION

In view of this, the present invention provides a stereotactic two-longitudinal-plane (hereinafter, "2L") linear ultrasonic transducer to orientate the moving direction (or trajectory) of a needle (or generally, various needle-like instruments). The two-longitudinal-plane linear transducer of the present invention can further be expanded to an "even-number"-longitudinal-plane linear (or curved) transducer.

The present invention develops the "incomplete mixing technique of bilateral soundwaves" to make soundwaves from the left side and the right side of transducing elements be partially mixed while preserving their independencies or differences. As a three-longitudinal-plane (hereinafter, 3L) linear transducer in prior arts carries corresponding three image planes, the 2L transducer in the present invention carries two image planes originally. The mixing of bilateral soundwave is used to reconstruct an extra central image plane in addition to the left and the right image plane in the 2L transducer. Herein, the mixing of the bilateral soundwaves mitigates a "blind zone" caused by a gap between two columns of transducing elements in the 2L transducer, so that the transducer can detect the soundwaves from the gap between the left plane and the right image plane, where a reconstructed central image plane lies in. Meanwhile, the preserved independencies of the bilateral soundwaves permit the transducer to generate stereotactic perception beyond single longitudinal image plane, which is lacked in a traditional 1L transducer.

Extending the rationale of the incomplete mixing technique, the transducing elements of the 2L transducer can be in various shapes and be overlapped in the elevation axis X (see FIG. 2A and FIG. 6), forming a "zipper" array. Specifically, viewing from the elevation axis, the left column of transducing elements in a zipper array may be interlocked with the right column of transducing elements, and the proportion of "elevational interlock" determines the level of mixing between bilateral soundwaves, and more importantly, the distance between the left and the right image planes. To be further, in order to design suitable shapes and sizes of the transducing element for detections in different clinical scenarios or tissue depths, the concept of elevation focus projection lines (see LR and LL in FIG. 8) are introduced, which is drawn by connecting the projection points of elevation focuses of the same side transducing elements. In other words, the elevation focus projection lines correspond to the highest energy density within a certain depth in the axial axis, which correlate to the elevational position of the detection image plane. Together, the present invention keeps stereotactic perception beyond the single image plane and permits reconstruction of a high quality extra central image plane over the gap in the 2L transducer.

Therefore, the present invention provides an ultrasonic transducer with a zipper array of transducing elements, which includes a tail and a head. A surface of the head is embedded with left column of transducing elements and right column of transducing elements, wherein at least one portion of each left transducing element overlaps each right transducing element in the elevation axis.

Other additional features can be found in the following embodiments. If suitable, each feature in each embodiment can be combined to realize different variations. Other objects, advantages, and novel features of the invention will become more apparent from the following detailed description when taken in conjunction with the accompanying drawings.

BRIEF DESCRIPTION OF THE DRAWINGS

FIG. 11E shows a schematic view illustrating the directions of the ultrasonic waves emitted by the ultrasonic transducer employing convex transducing elements and the beam width BW formed by superposition of soundwaves;

FIG. 11F shows a schematic view illustrating the directions of the ultrasonic waves emitted by the ultrasonic transducer employing a convex micro array of transducing elements and the beam width BW formed by superposition of soundwaves;

DETAILED DESCRIPTION OF THE EMBODIMENT

Figure 1A:
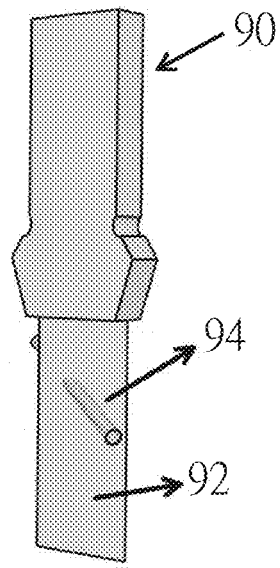
FIGS. 1A, 1B, and 1C show a needle navigation problem in the prior art.

Different embodiments of the present invention are provided in the following description. These embodiments are meant to explain the technical content of the present invention, but not meant to limit the scope of the present invention. A feature described in an embodiment may be applied to other embodiments by suitable modification, substitution, combination, or separation.

It should be noted that, in the present specification, when a component is described to have an element, it means that the component may have one or more of the elements, and it does not mean that the component has only one element, except otherwise specified.

Moreover, in the present specification, the ordinal numbers, such as "first" or "second", are used to distinguish a plurality of elements having the same name, and it does not mean that there is essentially a level, a rank, an executing order, or a manufacturing order among the elements, except otherwise specified. A "first" element and a "second" element may exist together in the same component, or alternatively, they may exist in different components, respectively. The existence of an element described by a greater ordinal number does not essentially means the existence of another element described by a smaller ordinal number.

In the present specification, describing a feature A "or" or "and/or" a feature B means that the feature A exists solely, the feature B exists solely, or the features A and B exist simultaneously; describing a feature A "and" a feature B means the features A and B exist simultaneously; the terms "include", "contain", "have", "comprise" means "include but not limited to", except otherwise specified.

Moreover, in the present specification, the terms, such as "top", "bottom", "left", "right", "front", "back", or "middle", as well as the terms, such as "on", "above", "under", "below", or "between", are used to describe the relative positions among a plurality of elements, and the described relative positions may be interpreted to include their translation, rotation, or reflection.

Moreover, in the present specification, when an element is described to be arranged "on" another element, it does not essentially mean that the elements contact the other element, except otherwise specified. Such interpretation is applied to other cases similar to the case of "on".

Moreover, in the present specification, the terms, such as "preferably" or "advantageously", are used to describe an optional or additional element or feature, and in other words, the element or the feature is not an essential element, and may be ignored in some embodiments.

Moreover, in the present specification, when an element is described to be "suitable for" or "adapted to" another element, the other element is an example or a reference helpful in imagination of properties or applications of the element, and the other element is not to be considered to form a part of a claimed subject matter; similarly, except otherwise specified.

Moreover, in the present specification, "about" a value means a range between ±10% of the value, in particular to a range of ±5% of the value.

Moreover, in the present specification, the terms, such as "system", "apparatus", "device", "module", or "unit", refer to an electronic element, or a digital circuit, an analogous circuit, or other general circuit, composed of a plurality of electronic elements, and there is not essentially a level or a rank among the aforementioned terms, except otherwise specified.

Moreover, in the present specification, two elements may be electrically connected to each other directly or indirectly, except otherwise specified. In an indirect connection, one or more elements, such as resistors, capacitors, or inductors may exist between the two elements. The electrical connection is used to send one or more signals, such as DC or AC currents or voltages, depending on practical applications.

Figure 2A:
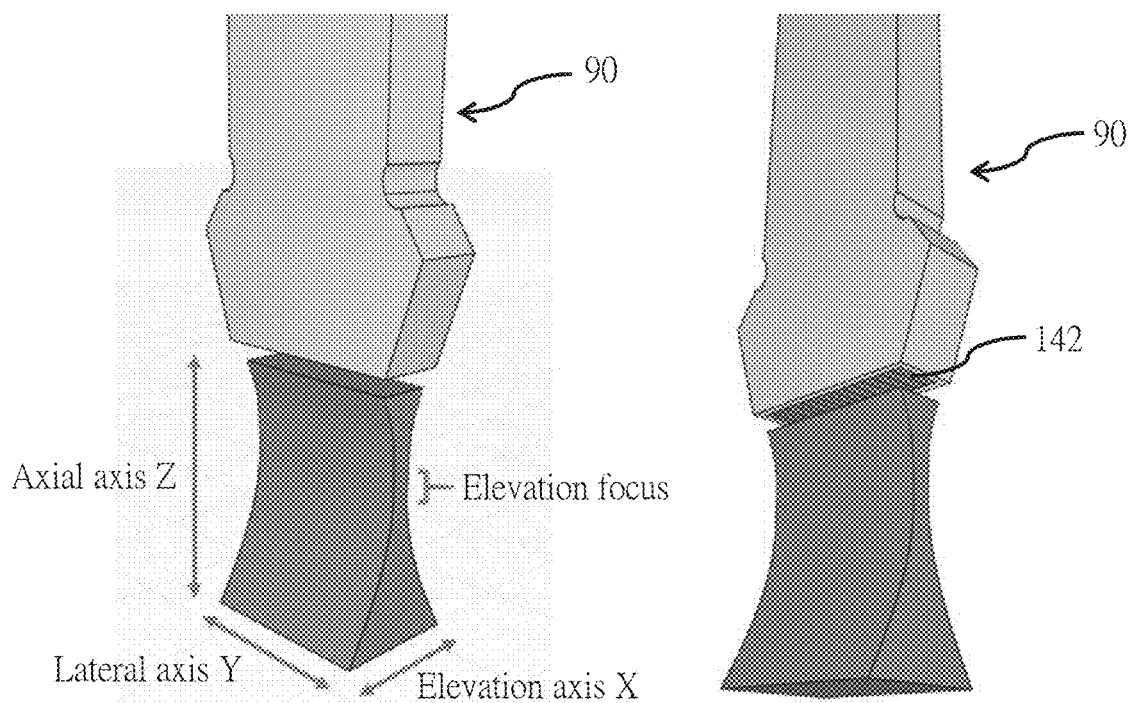
FIG. 2A shows a perspective view of the one-longitudinal-plane transducer and the sound energy coverage volume of the ultrasonic longitudinal detection plane.
Figure 2B:
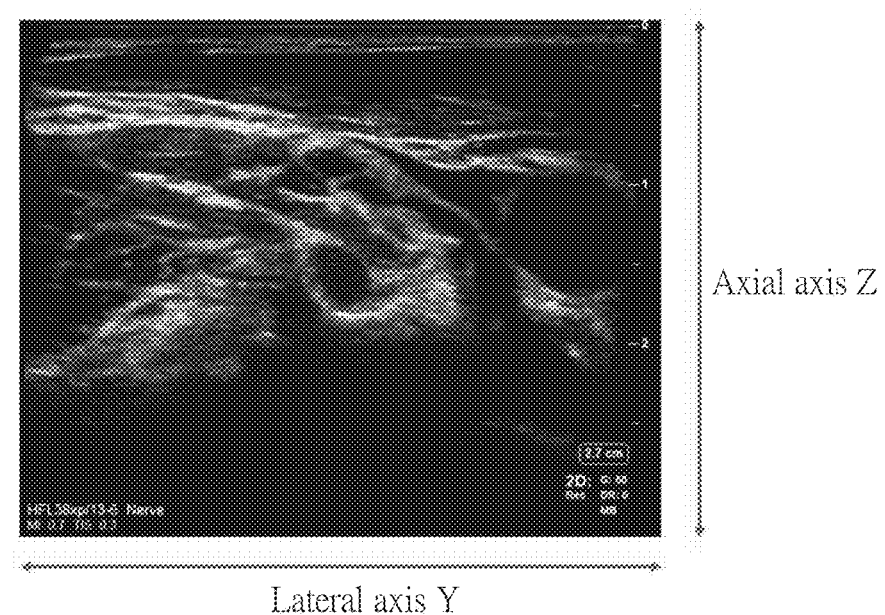
FIG. 2B shows an example of the ultrasonic longitudinal detection plane generated by the one-longitudinal plane transducer.
Figure 2C:
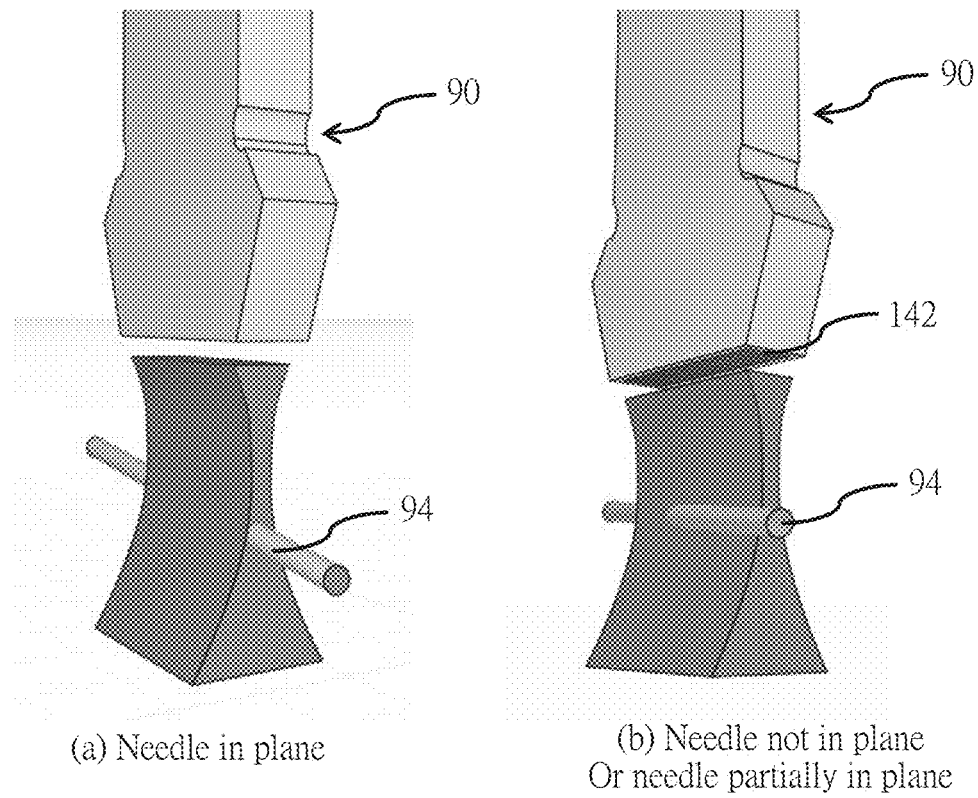
FIG. 2C shows (a) an example of a needle in plane, and (b) an example of a needle not in plane or a needle partially in plane.

FIG. 2A shows a perspective view of the sound energy coverage volume of a one-longitudinal-plane transducer 90, which constructs the ultrasonic longitudinal detection plane in FIG. 2B. Herein, an example of a needle "in plane" is shown in FIG. 2C (a), and a contrary example of a needle "not in plane" or a needle "partially in plane" is depicted in FIG. 2C(b).

Figure 3A:
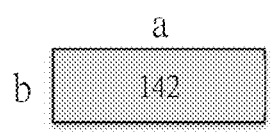
FIG. 3A shows a schematic diagram of a rectangular transducing element in prior arts.

FIG. 3A shows the shape of the transducing element 142. In the one-longitudinal-plane transducer 90, rectangular transducing elements 142 are arranged in an array of one column and N rows (1×N). The relation between the rectangular transducing elements 142 and the ultrasonic beam can be defined by the following three perpendicular axes:

(1) an elevation axis X, also known as the short axis of the transducer, which extends across one column of rectangular transducing elements 142.

(2) a lateral axis Y, also known as the long axis of the transducer, which extends across N rows of rectangular transducing element 142.

(3) an axial axis Z, which extends along the emitting direction of the ultrasonic beam.

The rectangular transducing element 142 can emit ultrasonic beam, which transmits along a medium, and once it contacts a target object in the medium, a reflecting soundwave (or echo) turns back and is received by the rectangular transducing element 142. Then, by signal analysis of the echo, the ultrasonic longitudinal detection plane (which is a plane lying in the lateral axis Y and the axial axis Z of the transducer, as shown in FIG. 2B) is depicted by a two-dimensional gray scale image.

Moreover, as shown in FIG. 2A, when the ultrasonic beam transmits along the axial axis Z, the sound energy mainly lies in the beam width (BW) of the elevation axis X. Based on the natural converging or diverging phenomenon of the ultrasonic beam transmission, the beam width BW varies along the depth or the axial axis Z. At the depth of the elevation focus EF, the beam width becomes the thinnest one, and it is called the beam width at the elevation focus BWEF. The beam width at a depth shallower than the elevation focus EF is called the beam width in the elevation near field BWENF. The beam width at a depth deeper than the elevation focus EF is called the beam width in the elevation far field BWEFF. When a target object locates within the beam width BW of a certain depth, it reflects soundwaves (or generates "echoes") and is shown in the detection plane, and the case is called "the object (is) in plane"; in the contrary, when the target object locates outside the beam width BW of a certain depth, it cannot reflect soundwaves and cannot be shown in the detection plane, which is called "the object (is) not in plane". Therefore, the ultrasonic longitudinal detection plane not only spatially corresponds to the plane defined by the lateral axis Y and the axial axis Z, but is also defined by a thickness in the elevation axis X, which is called the elevation width EW, the elevation thickness ET, or the slice thickness ST, as shown in FIG. 2A.

When guiding a needle, as in an example (a) in FIG. 2C, the clinical term "needle (is) in plane" means the case where "the possible maximal part of the needle" is optimally adjusted within the beam width BW or the slice thickness ST of the detection plane; in the contrary, as in an example (b) in FIG. 2C, the so-called "needle (is) not in the plane" or "needle (is) partially in the plane" typically means that the needle has only a section been adjusted within the beam width BW, and the detection plane can only show the oblique sectional view of the needle.

Figure 1B:
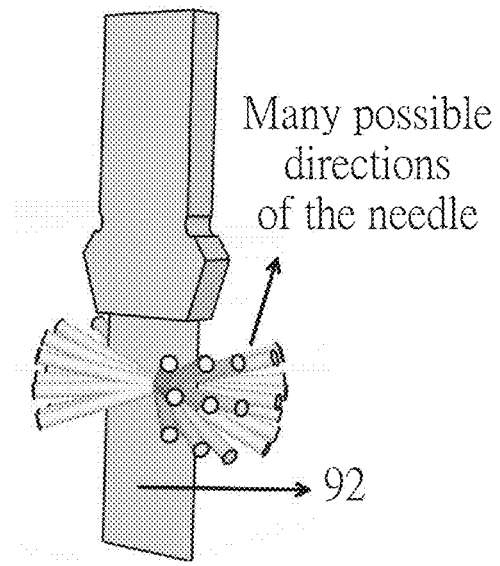
Figure 1C:
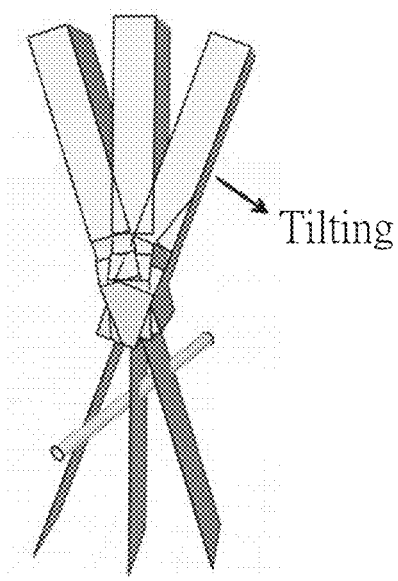

Within the beam width BW or the slice thickness ST of a certain lateral axis Y coordinate and axial axis Z coordinate in the detection plane, two different objects with different elevation axis X coordinates will be shown as the same object. This means that the beam width BW determines the elevation resolution ER. Since the one-longitudinal-plane transducer 90 has only one column of transducing elements 142 in the elevation axis, according to the principle of linear antenna array, it is directional-blinded in the elevation axis and cannot distinguish the mirror moving directions of the needle during needle navigation, as depicted in FIG. 1B.

On the contrary, the one-longitudinal-plane transducer 90 has N rows of transducing elements 142 in the lateral axis Y, according to the principle of linear antenna array, because N≥2 and the target object only presents at one side of the linear antenna array, it can distinguish different lateral axis coordinates.

The beam width or the elevation thickness of the detection plane is mainly determined by transducing element's shape, transducing element's size (typically, a transducing element is a rectangular element with its size of 4×0.3 mm to 12 mm×0.3 mm, for example), acoustic frequency, acoustic lens' focus, and so on. If the element has a smaller length a (marked in FIG. 3A), it has a smaller beam width as well as a better elevation resolution. The acoustic lens can further adjust the ultrasonic beam convergence and hence the elevation focus. By definition, the thinnest beam width at the elevation focus provides the best elevation resolution, and makes it easiest to distinguish two elevational different objects.

Figure 3B:
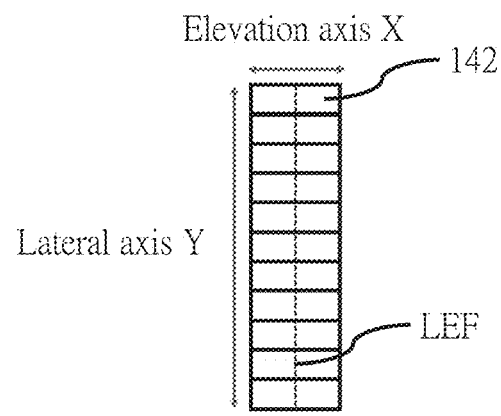
FIG. 3B shows a schematic diagram of the linear alignment of the rectangular transducing elements of the one-longitudinal-plane transducer.
Figure 3C:
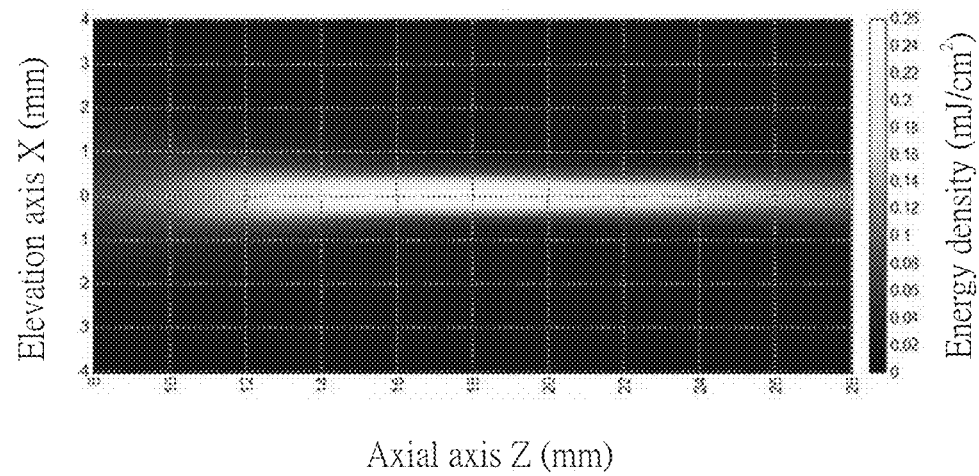
FIG. 3C shows a measurement diagram of the beam energy density.
Figure 3D:
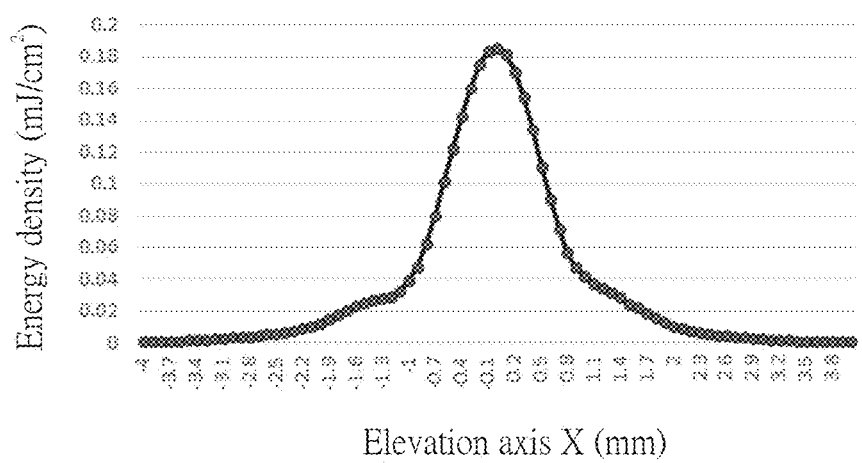
FIG. 3D shows a curve diagram of the elevation sound energy density curve diagram of the elevation sound energy density of the rectangular transducing element of the one-longitudinal-plane transducer.

FIG. 3B shows a schematic diagram of the rectangular transducing element 142 of the one-longitudinal-plane transducer 90. FIG. 3C shows a measurement diagram of the beam energy density, wherein the horizontal axis is the axial axis Z, and the vertical axis is the elevation axis X. FIG. 3D shows the elevation sound energy density curve ESEDC of the rectangular transducing element 142 of the one-longitudinal-plane transducer 90, which is the sectional view of the elevation energy density at a certain axial depth (or a certain axial axis coordinate).

The rectangular transducing elements 142 of the one-longitudinal-plane transducer 90 can emit ultrasonic beam carrying a symmetric, non-skewed bell shaped curve energy density along its elevation axis X, as shown in FIG. 3D. The curve's apex corresponds to the elevation focus of a certain axial depth, where the energy density is the highest one. The dotted line in FIG. 3B is the "elevation focus projection line" LEF, which represents the projected positions of the elevation focuses on the surface of the rectangular transducing element 142. It is noted that, since the energy density curve of the rectangular transducing element 142 is symmetric in the elevation axis, the elevation focus projection line LEF also locates in the middle of the elevation thickness of the detection plane, or overlaps equal-area bisector in the elevation axis of the rectangular transducing element 142.

Figure 4:
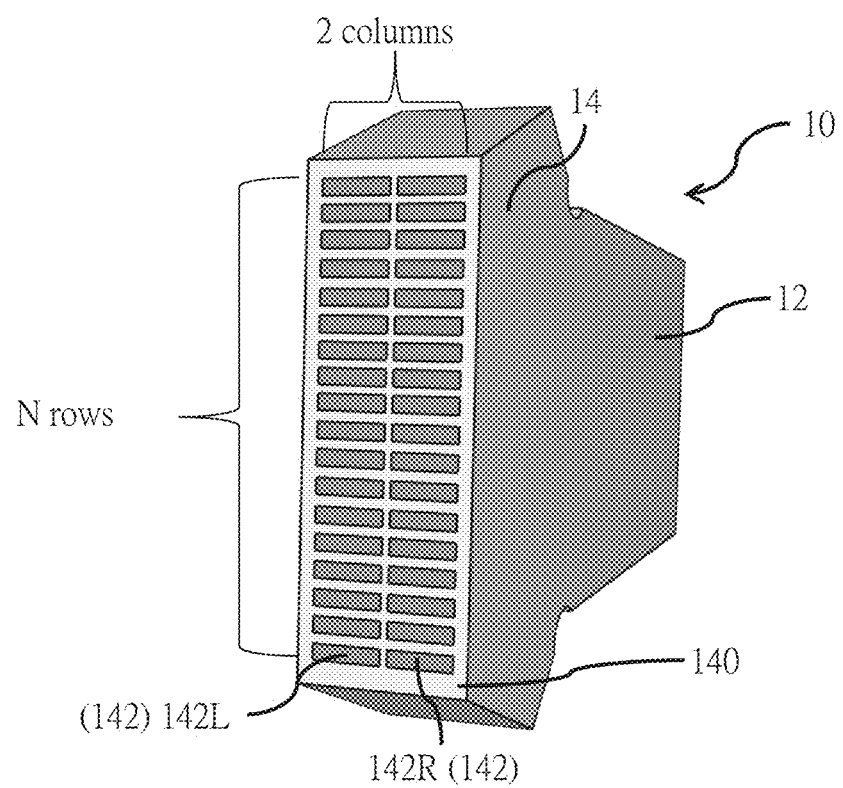
FIG. 4 shows a perspective view of the two-longitudinal-plane linear ultrasonic transducer according to one embodiment of the present invention.

FIG. 4 shows a perspective view of the two-longitudinal-plane (2L) linear ultrasonic transducer 10 according to one embodiment of the present invention.

The ultrasonic transducer 10 of the present invention has a tail 12 and a head 14. The tail 12 can be held by the user or a robotic arm. The head 14 has a surface 140 embedded with (acousto-electric or piezo-electric) transducing element 142. In other words, the transducing elements 142 mainly appear on the surface 140, at most a small portion protrudes out of the surface 140. During an operation, the surface 140 may be in contact with the surgical site of the patient. In other embodiments, other components may be arranged on the surface 140, for example, an acoustic lens, a matching layer, or a covering layer, and in these cases, what is closely in contact with the surgical site are these components. The transducing element 142 can convert electronic signal(s) into ultrasonic wave(s), or convert the reflected ultrasonic wave(s) into electronic signal(s). The transducing element 142 may be realized by numerus acoustoelectric converting technologies, include but is not limited to (bulk) piezoelectric material, piezoelectric micro-machined ultrasonic transducer (PMUT), capacitive micro-machined ultrasonic transducer (CMUT) technologies.

According to the present invention, the transducing elements 142 of the ultrasonic transducer 10 are arranged in an array of two columns times N rows (2×N). In other embodiments, the 2×N array may be divided into tighter M×N arrays, and then a circuit, a chip, or a software may be used to cancel their divisions or merge their electronic signals, so as to achieve a substantially equivalent element shape or a substantially equivalent elevation sound energy density curve ESEDC as in the 2×N array of the present invention.

Therefore, the aforementioned array of transducing elements 142 consists of the left transducing elements 142L and the right transducing elements 142R, respectively configured to form a left ultrasonic longitudinal detection plane PL and a right ultrasonic longitudinal detection plane PR. The longitudinal detection plane may be called "longitudinal plane" hereinafter.

The emitting and receiving mechanisms of the left transducing elements 142L and the right transducing elements 142R can include one or more of the following modes:
(i) using one side to emit the ultrasonic beam, and using the same side to receive the echo of the ultrasonic beam;
(ii) using one side to emit the ultrasonic beam, and using another side to receive the echo of the ultrasonic beam;
(iii) using one side to emit the ultrasonic beam, and using both two sides at the same time to receive the echo of the ultrasonic beam;
(iv) using both two sides at the same time to emit the ultrasonic beam, and also using both two sides at the same time to receive the echo of the ultrasonic beam; or
(v) using both two sides at the same time to emit the ultrasonic beam, and using one side to receive the echo of the ultrasonic beam.

Figure 5A:
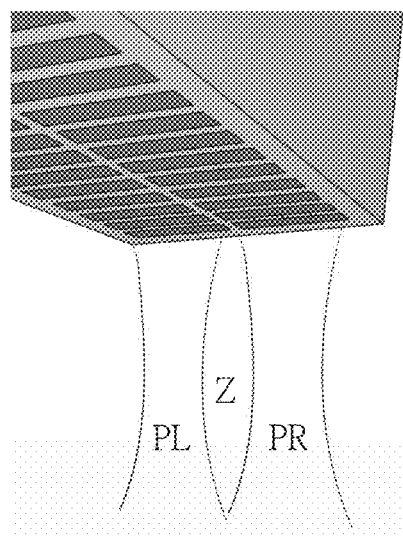
FIGS. 5A and 5B show schematic views illustrating the operation of the ultrasonic transducer of FIG. 4.
Figure 5B:
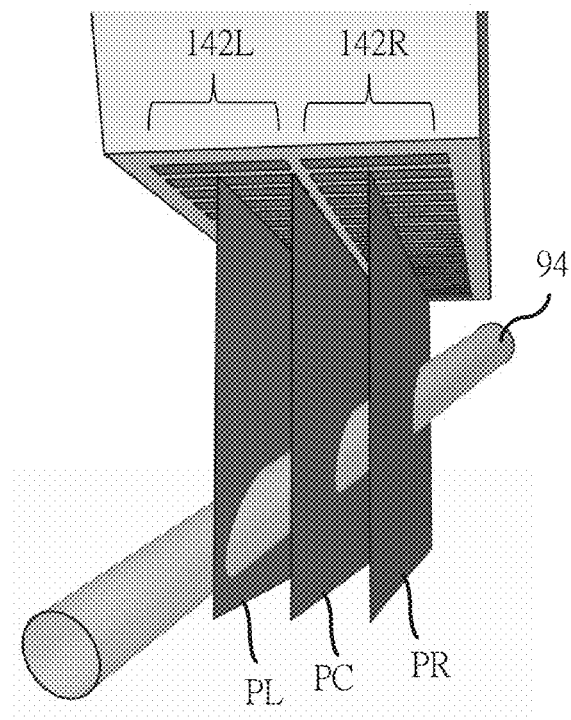

FIGS. 5A and 5B show schematic views illustrating the operation of the ultrasonic transducer 10 of FIG. 4.

In the embodiments of FIGS. 5A and 5B, a bilateral-equal-time-distance central ultrasonic longitudinal detection plane (may be called the "central plane" hereinafter) PC to be built or a blind zone Z to be minimized exists between the left ultrasonic longitudinal detection plane PL and the right ultrasonic longitudinal detection plane PR. The system of the ultrasonic transducer 10 of the present invention can perform time domain analysis on the echo signal to construct the central plane PC, since the signal transmission time from the central plane PC to the left transducing element 142L is equal to the signal transmission time from the central plane PC to the right transducing element 142R.

Figure 6:
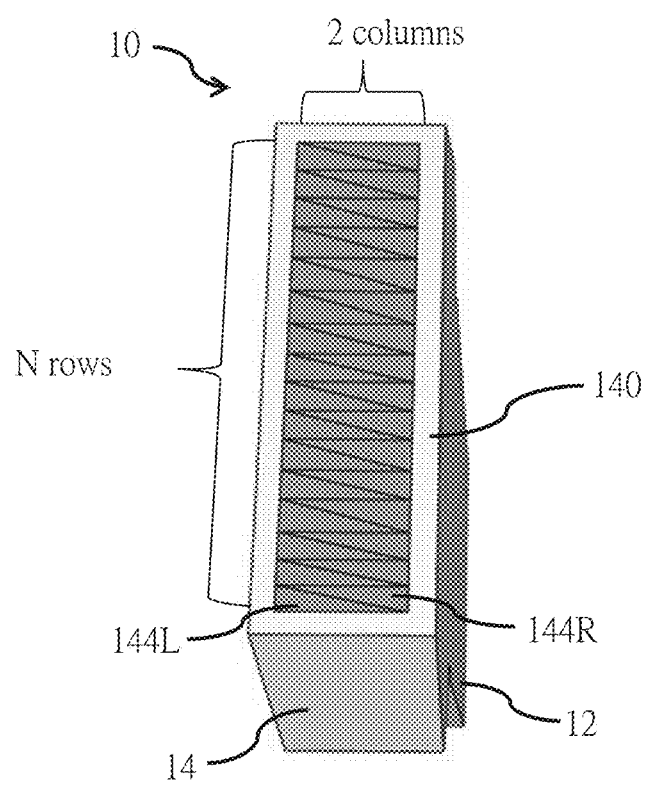
FIG. 6 shows a perspective view of the ultrasonic transducer with a zipper array of transducing elements according to one embodiment of the present invention.

FIG. 6 shows a perspective view of the ultrasonic transducer 10 with a zipper array of transducing elements 144 according to one embodiment of the present invention.

In the embodiment of FIG. 6, the non-rectangular transducing elements 144 are designed to be different from the rectangular transducing elements 142 shown in FIG. 4 as the non-rectangular transducing elements 144 cannot be arranged in an elevational-non-overlapping two-column-N-row (2×N) array; instead, they form a zipper or an elevational-overlapping array. In particular, at least one portion of each left transducing element 144L overlaps each right transducing element 144R in the elevation axis X. Herein, a left transducing element 144L is defined to have a larger left area and a smaller right area, for example, it may have a triangular shape with its area reduced from left to right; a right transducing element 144R is defined to have a larger right area and a smaller left area, for example, it may have a triangular shape with its area reduced from right to left. Moreover, each left transducing element 144L and each right transducing element 144R is symmetrically interlocked with (or is matched to or is chimeric with) each other in terms of their shapes. Furthermore, each left transducing element 144L is complementary to each right transducing element 144R in terms of their shapes to form a rectangle. As shown in FIG. 6, each left transducing element 144L is a triangle with a rightward tip, and each right transducing element 144R is a triangle with a leftward tip, and they are complementary to each other to form a rectangle with minimal gaps between the left transducing element 144L and the right transducing element 144R. However, it should be noted that, the chimerism between the left and the right side transducing elements not necessarily forms a rectangle, but is merely an example.

In the embodiment of FIG. 6, similarly to the embodiment of FIG. 5A, the left transducing elements 144L is configured to form a left ultrasonic longitudinal detection plane PL, and the right transducing elements 144R is configured to form a right ultrasonic longitudinal detection plane PR. In particular, in the elevation axis, the left ultrasonic longitudinal detection plane PL can be defined at the elevation focus of the left transducing elements 144L, or the position having the strongest ultrasonic beam energy emitted by the transducer or the strongest echo received from the target object; and the right ultrasonic longitudinal detection plane PR can be defined at the elevation focus of the right transducing elements 144R, or the position having the strongest ultrasonic beam energy emitted by the transducer or the strongest echo received from the target object.

Figure 8:
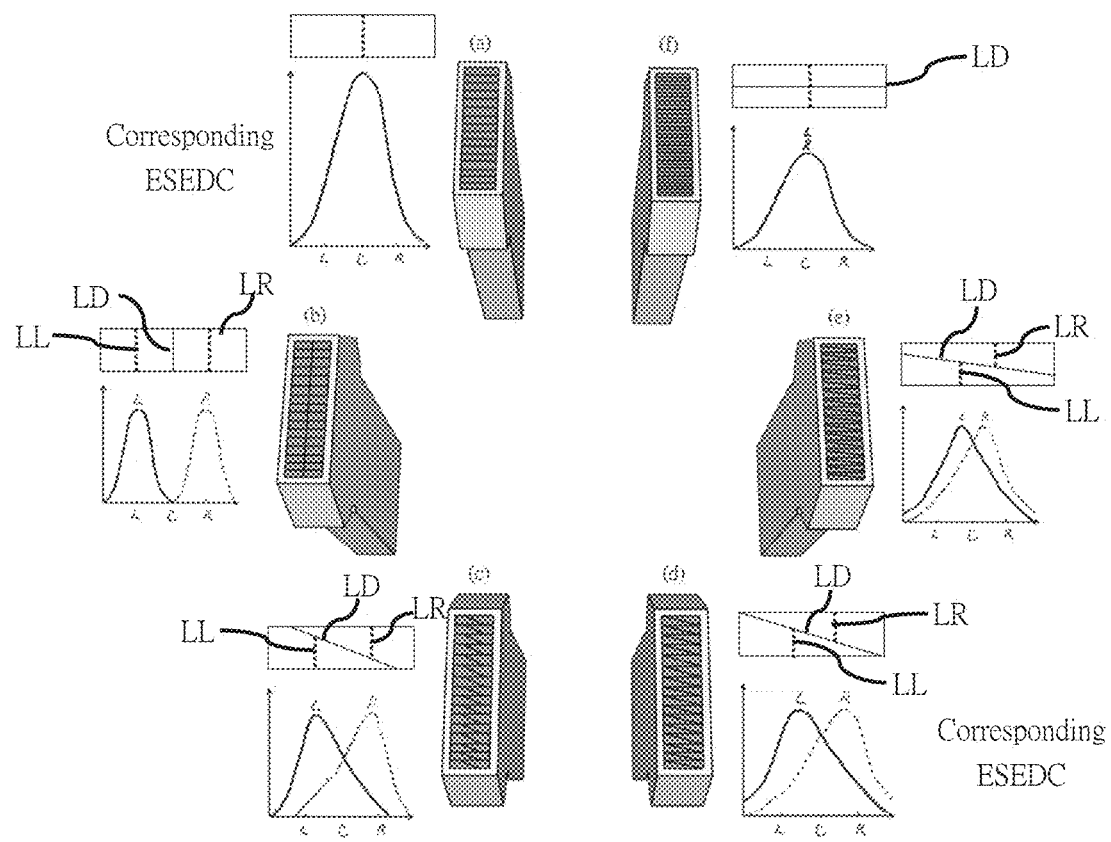
FIG. 8 shows a perspective view of transducing elements of various shapes and their corresponding "elevation sound energy density curve" within a specific range on the axial axis.

In example of FIG. 6 and FIG. 8 (d), each left transducing element 144L is marked by a "left elevation focus projection line LL", and each right transducing element 144R is marked by a "right elevation focus projection line LR". According to the principle of the present invention, the central position of the left ultrasonic longitudinal detection plane PL is defined at the position of the "left elevation focus projection line LL", and the central position of the right ultrasonic longitudinal detection plane PR is defined at the position of the "right elevation focus projection line LR". Therefore, the distance between the central position of the left ultrasonic longitudinal detection plane PL and the central position of the right ultrasonic longitudinal detection plane PR is determined by the distance between the left elevation focus projection line LL and the right elevation focus projection line LR.

Figure 7A:
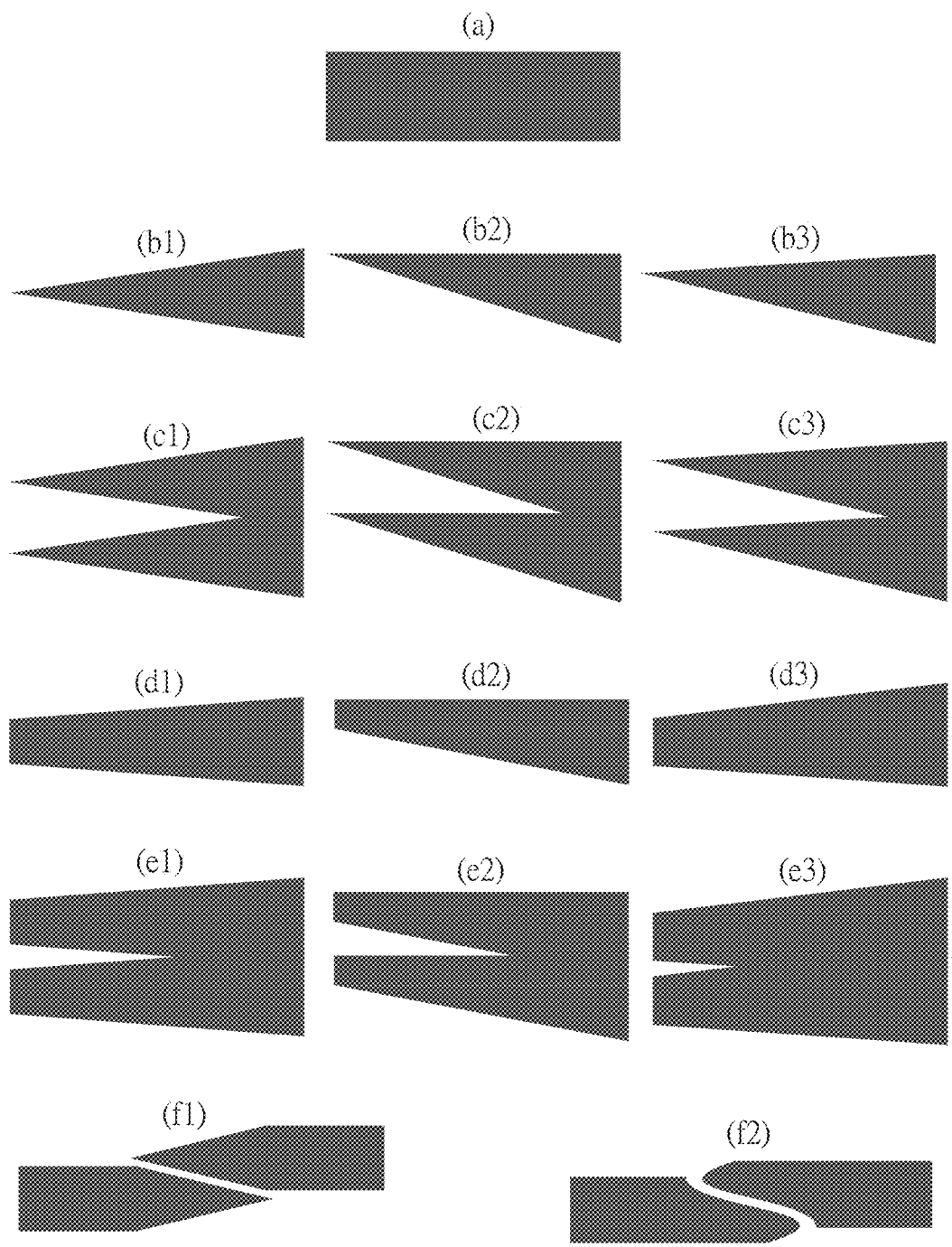
FIGS. 7A and 7B show planar views of transducing elements of various shapes of the present invention.
Figure 7B:
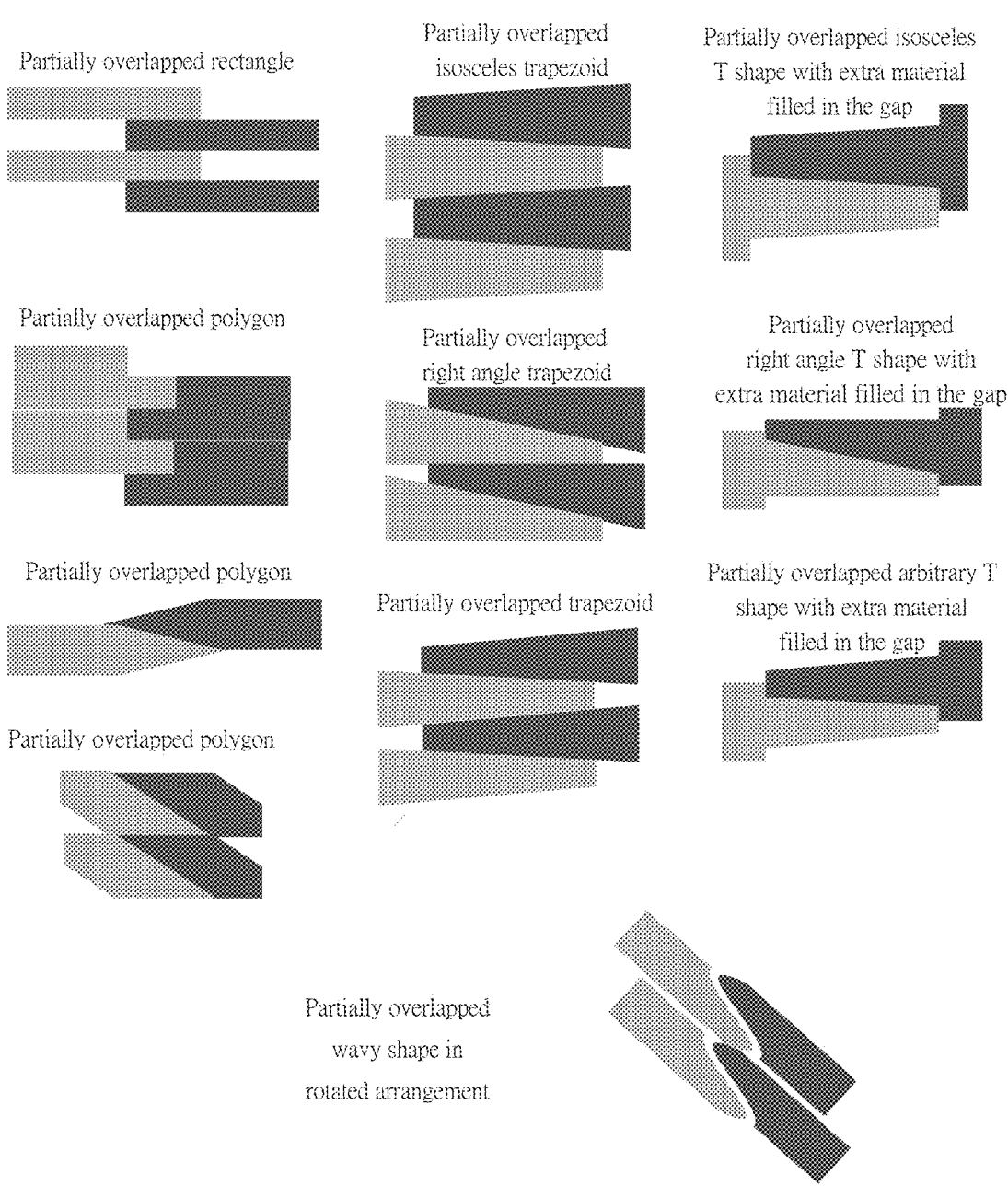
Figure 7C:
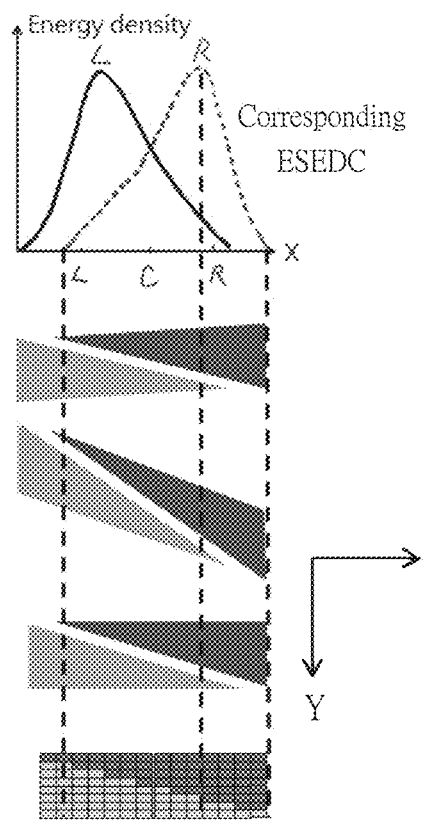
FIG. 7C shows an example illustrating that transducing elements of different shapes can generate a substantially equivalent energy density curve.
Figure 7D:
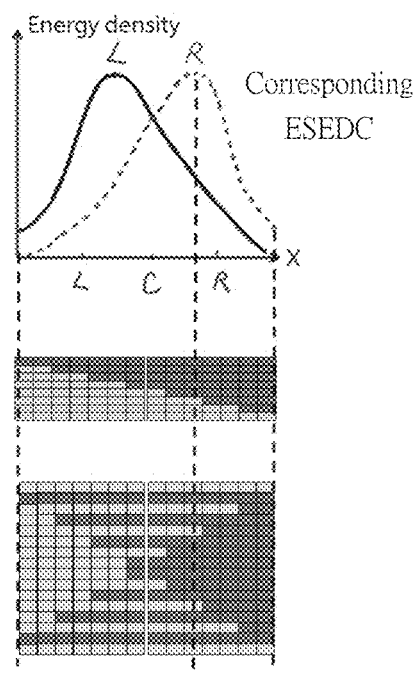
FIG. 7D shows an example illustrating that the conductive electrodes of the M×N array can be connected in parallel to realize the same-ratio zipper shape to generate a substantially equivalent energy density curve.

FIGS. 7A and 7B show planar views of various shapes of transducing element 144 of the present invention. FIG. 7C shows an example in which different shapes of transducing elements can generate substantially equivalent energy density curves. FIG. 7D shows an example of generating a substantially equivalent energy density curve by paralleling the electrical conductors of an equal-scale (proportional) shapes of M×N array.

As shown in FIG. 7A, the transducing element 144 (for example, each left transducing element 144L or each right transducing element 144R) are conventionally rectangular as in case (a), but it may be non-rectangular in accordance with the present invention. In addition, the present invention cites several non-rectangular shapes that can minimize gaps (or blind zone Z) between the transducer elements 144 in the zipper-like staggered arrangement. The non-rectangular shapes may include (b1) an isosceles triangle, (b2) a right triangle, (b3) any other triangle, (c1) multiple isosceles triangle comb, (c2) multiple right triangle comb, (c3) multiple any other triangle comb, (d1) an isosceles trapezoid, (d2) a right-angled trapezoid, (d3) any other trapezoid, (e1) multiple isosceles trapezoid comb, (e2) multiple right-angled trapezoid comb, (e3) multiple any other trapezoid comb, (f1) chimeric polygon, (f2) chimeric wavy, etc. Among them, a wavy shape may be composed of arcs or parabolas. The above-mentioned various shapes may be appropriately interlocked and be complementary (or chimeric) to each other, in order to form a rectangle or other possible polygons, thereby forming a tight arrangement without leaving gaps or blind zone Z between the left transducing element 144L and the right transducing element 144R.

For sure, various shapes may also be partially interlocked, as shown in FIG. 7B, wherein the examples of various partially interlocked arrays have been marked in FIG. 7B.

FIG. 8 shows a perspective view of transducing elements of various shapes and their corresponding "the elevation sound energy density curve ESEDC (or referred to as "curve" somewhere in this description) within a specific range of the transducer axial axis Z, wherein the horizontal axis on each curve ESEDC indicates the positions on the elevation axis X of the transducer (only roughly indicates the left L, the middle C, and the right R), and the vertical axis indicates the energy density.

In FIG. 8:

Example (a) is a one-longitudinal-plane transducer (hereinafter, 1L transducer), which has a curve ESEDC in symmetric bell shape with single peak;

Example (b) is a two-longitudinal-plane transducer (or 2L transducer), which has left and right rectangular transducing elements, corresponding to the left and right curves ESEDCs respectively, and the distribution of each curve also presents a symmetrical bell shape, and since the curves do not completely overlap each other, the stereotactic perception in the horizontal axis (corresponds to the elevation axis) can be built;

Example (c) is a transducer with zipper array of trapezoid transducing elements of the present invention, which has left and right transducing elements, corresponding to the left and right curves ESEDCs respectively, and the distribution of each curve presents a slightly skewed bell shape, and since the curves do not completely overlap each other, this can bring about stereotactic perception in the left and right direction or in the direction of the elevation axis, comparatively to example (b), and the "incomplete mixing technique of bilateral soundwaves" of the present invention can be achieved to control the trade-off between the stereotactic perception and the signal strength of the central plane;

Example (d) is a transducer with a zipper array of right triangle transducing elements of the present invention, wherein its skewed left and right curves ESEDCs are similar to the curves of the example (c), and the positions of the left elevation focus projection line LL and the right elevation focus projection line LR are estimated by the peaks of the left and the right curves, respectively, which are further closer to each other than that of example (c);

Example (e) is another transducer with a zipper array of trapezoid transducing elements of the present invention, wherein the positions of the left elevation focus projection line LL and the position of the right elevation focus projection line LR are even closer, and their distance can also be estimated by the peaks of the left and right curves ESEDCs;

Example (f) is another 1L transducer as a comparative case. In comparison to example (a), the transducing elements in example (f) have the same elevation dimension, but a smaller lateral dimension. It can be observed that the contact line LD gradually "rotates" from the vertical state of the example (b) to the horizontal state of the example (f), and correspondingly, the peaks of both left and right curves ESEDCs gradually transform from the separated state of the example (b) to a fully overlapping state.

According to numerous examples in FIGS. 7A to 7D and FIG. 8, different shapes of transducing elements can generate the same or substantially equivalent energy density curve ESEDC. In other words, according to the present invention, in order to realize a certain energy density curve ESEDC, a variety of equivalent shapes can be generated through reverse engineering, and almost each one can be selected as the shape of transducer element. As previously discussed in FIG. 7C and FIG. 7D, a circuit of an M×N array can be connected in parallel to achieve proportional shape of a 2×N array with substantially equivalent elevation sound energy density curve ESEDC. In other words, an equivalent proportional shape can be realized by parallel circuits of the M×N array. The analysis of various equivalent proportional shapes may refer to the examples in FIG. 7C and FIG. 7D.

Figure 9:
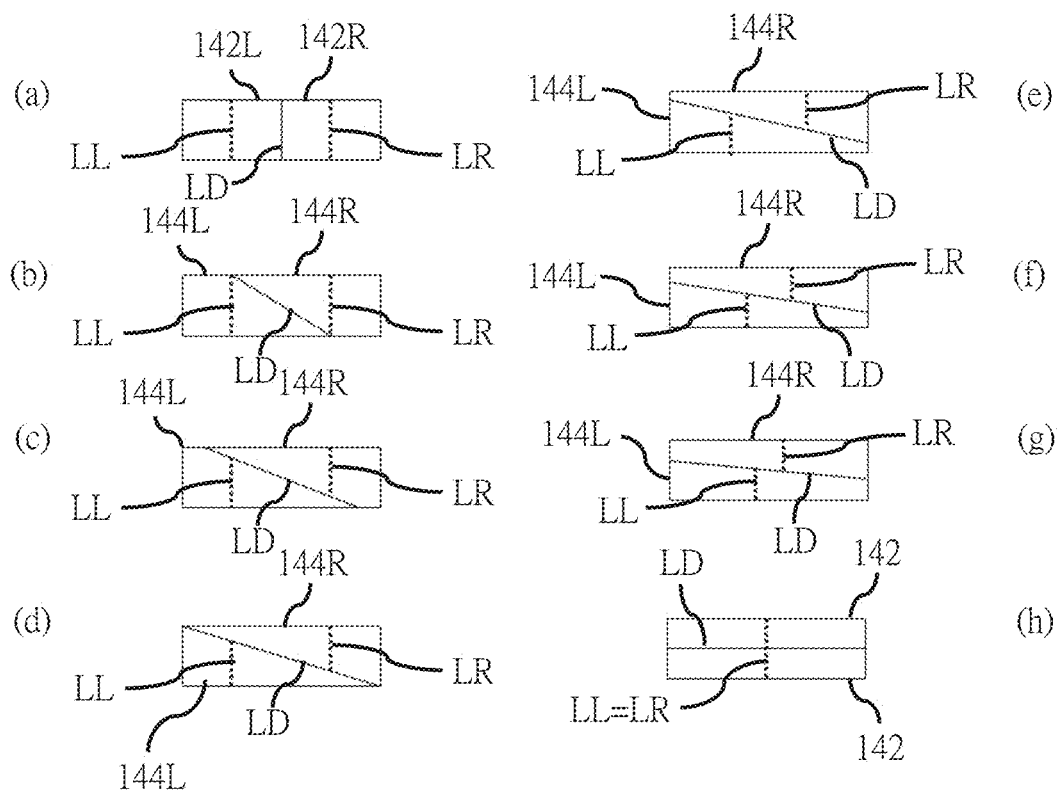
FIG. 9 shows plan views of various shapes of transducing elements of the present invention.

FIG. 9 shows plan views of various shapes of transducing elements 144 of the present invention.

In FIG. 9, each left transducing element 144L and each right transducing element 144R are interlocked and complementary to each other at the contact line LD to form a rectangle. As described in the embodiment of FIG. 6, the left transducing elements 144L is defined with a left elevation focus projection line LL, and the right transducing elements 144R is defined with a right elevation focus projection line LR. The contact line LD is perpendicular to the elevation axis of a transducer in Shape (a), and it is gradually rotated though Shape (b) to Shape (g), and eventually appears parallel to the elevation axis in Shape (h). Along this "rotation" of the line LD from Shape (a) to Shape (h), the distance between the left elevation focus projection line LL and the right elevation focus projection line LR is gradually reduced.

Moreover, as described in the embodiment of FIG. 6, according to the principles of the present invention, the position of the left ultrasonic longitudinal detection plane PL is estimated by its elevation focus and the position of the left elevation focus projection line LL; the position of the right ultrasonic longitudinal detection plane PR is also estimated by its elevation focus and the position of the right elevation focus projection line LR. However, the position of the elevation focus projection line of transducing element of different shape may not exactly be the position of the detection plane, which depends on numerous factors that affects acoustic focusing.

In FIG. 9, the position of the elevation focus projection line can be used to estimate the position of the detection plane, and in this way, shape (a) has the farthest distance between the left ultrasonic longitudinal detection plane PL and the right ultrasonic longitudinal detection plane PR, and in the elevation axis, the spatial span of the stereotactic perception is of the greatest but the signal of the central plane PC to be built is of the weakest; on the contrary, shape (h) is degenerated into an one-longitudinal-plane ultrasonic transducer, so the signal from the central plane PC is of the strongest, but it losses the abilities of coordinate recognition and stereotactic perception in the elevation axis.

By controlling the angle of the contact line LD, the interlocked shapes and the interlocked levels for different left and right elements are determined, and a specific level of balance is achieved between the scope of stereotactic perception and the signal intensity of the central plane PC to be built, and thereby help confirm the moving direction of the needle. Besides, the contact line LD may be a straight line, a polyline, or any other curve, such that the interlocked left and right elements can form numerous shapes with substantially equivalent acoustic mixing effect, or even provide special effect. The shapes formed by interlocking may be a rectangle or any other polygon shape.

Figure 10:
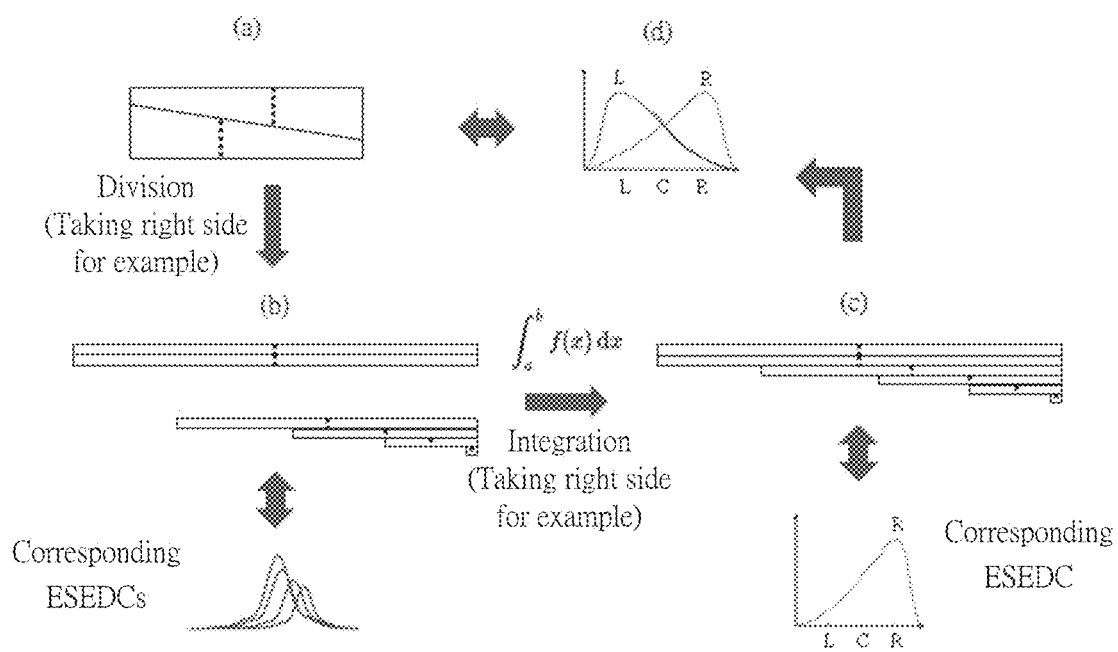
FIG. 10 shows a schematic view illustrating the analysis of transducing elements 144 by principles of calculus and analytic geometry.

FIG. 10 shows a schematic view illustrating the analysis of transducing elements 144 by principles of calculus and analytic geometry. In FIG. 10:

Step (a) shows an example of a zipper array of trapezoid transducing elements 144;

Step (b) is to divide one-side trapezoid transducing element 144 into an infinite number of tiny rectangles of different sizes based on the principle of calculus, each tiny rectangle corresponds to its own elevation sound energy density curve ESEDC (which may be referred to FIG. 3D), which is a symmetric curve without skew;

Step (c) shows the result after superposing the elevation sound energy density curves ESEDCs corresponding to the tiny rectangles arranged according to their positions on elevation axis, wherein the horizontal axis indicates the positions on the elevation axis (by roughly marking left-aligned L, middle-aligned C, and right-aligned R), and its vertical axis indicates the energy density, which is an asymmetric skew curve; and Step (d) shows the respective elevation sound energy density curves ESEDCs of the left transducing element 144L and the right transducing element 144R derived by the aforementioned principles of calculus and analytic geometry.

Figure 11A:
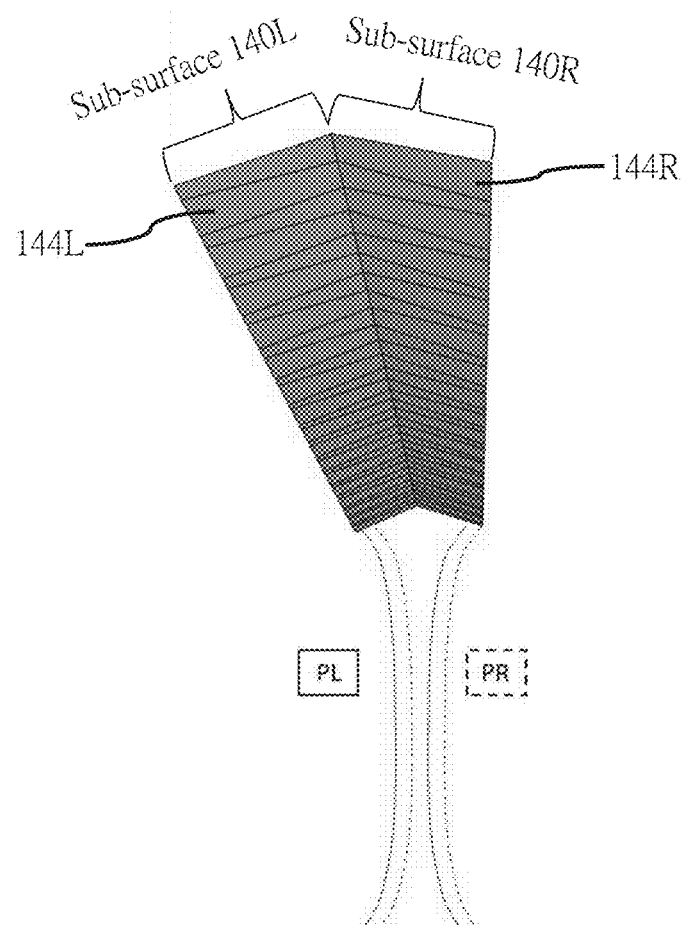
FIG. 11A shows a schematic view of the ultrasonic transducer having a folded structure according to one embodiment of the present invention.
Figure 11B:
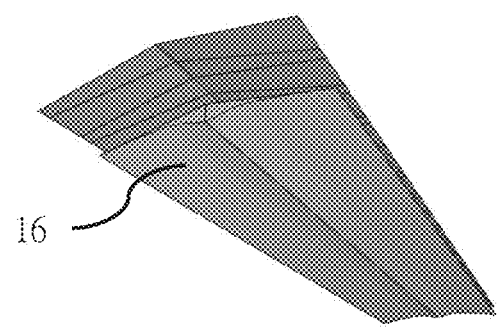
FIG. 11B shows a schematic view of the ultrasonic transducer having a folded structure working with an acoustic lens according to one embodiment of the present invention.
Figure 11C:
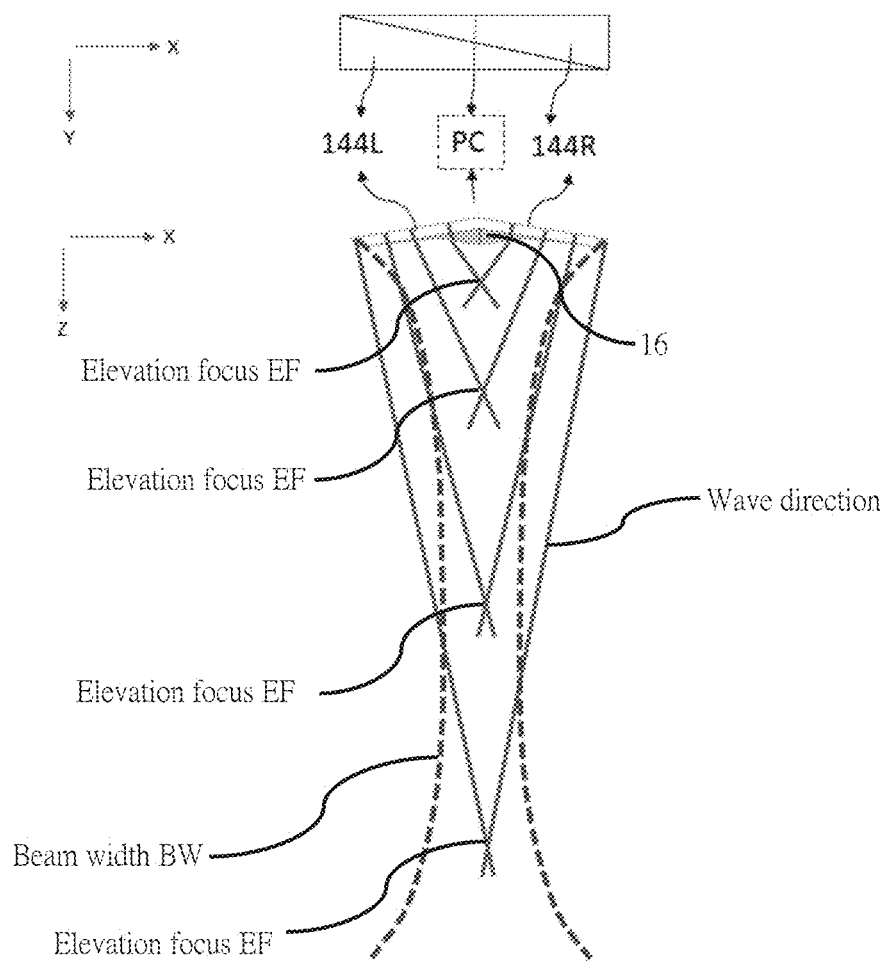
FIG. 11C shows a schematic view illustrating the directions of the ultrasonic waves emitted by the ultrasonic transducer in FIG. 11B, and the elevation focuses EF and the beam width BW formed by superposition of soundwaves.
Figure 11D:
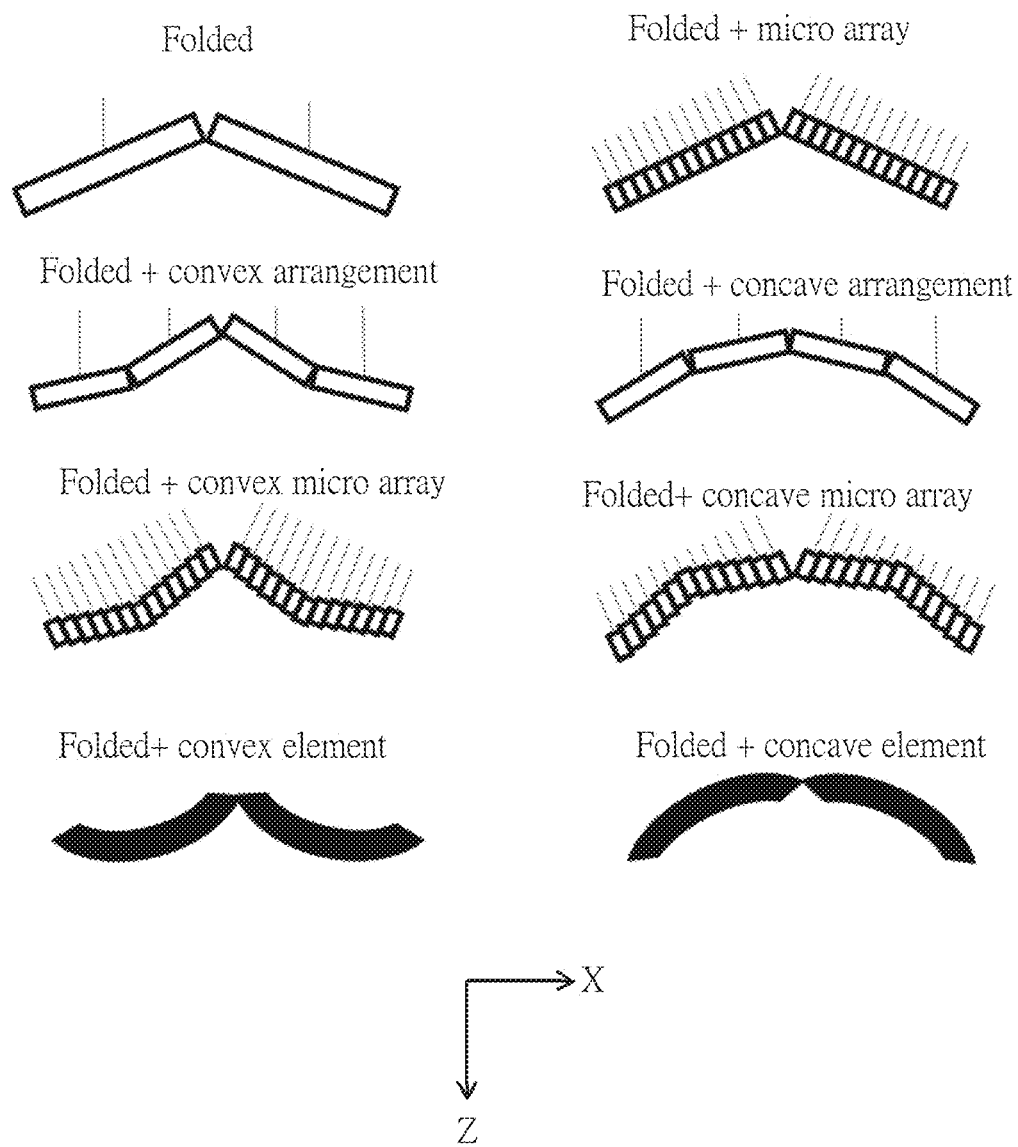
FIG. 11D shows various embodiments of the folded zipper array of transducing elements embedded on the folded sub-surface of the ultrasonic transducer.
Figure 11G:
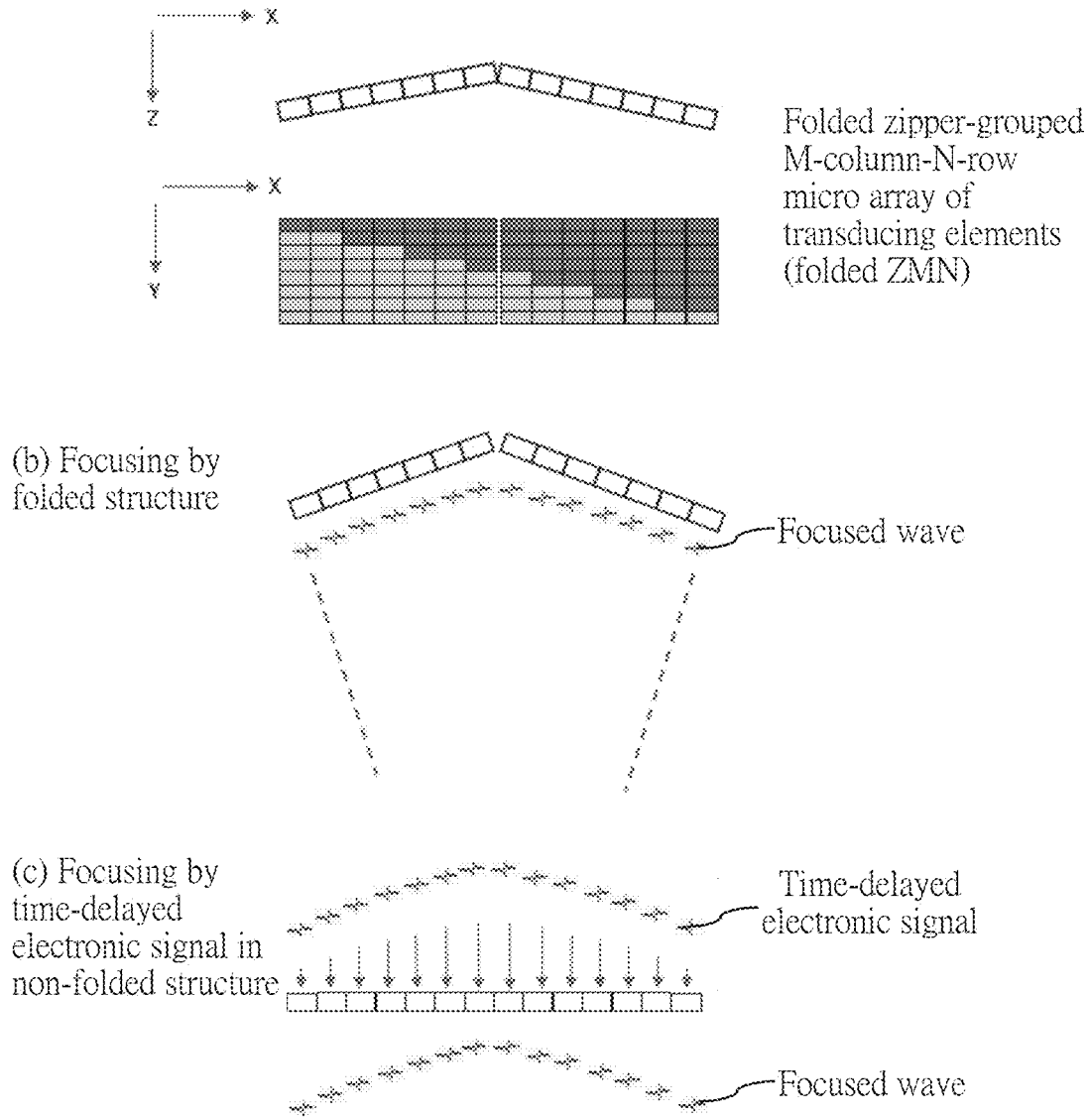
FIG. 11G shows a schematic view of a zipper-grouped M×N array of transducing elements (ZMN) with electronic focusing of the present invention, which substantially equivalently replaces focusing by folded structure and/or focusing by an acoustic lens.

FIG. 11A shows a schematic view of the ultrasonic transducer having a folded structure according to one embodiment of the present invention. FIG. 11B shows a schematic view of the ultrasonic transducer having a folded structure working with an acoustic lens 16 according to one embodiment of the present invention. FIG. 11C shows a schematic view illustrating the directions of the ultrasonic waves emitted by the ultrasonic transducer in FIG. 11B, and the elevation focuses EF and the beam width BW formed by superposition of soundwaves. FIG. 11D shows various embodiments of the folded zipper array of transducing elements 140 embedded on the folded sub-surface 140 of the ultrasonic transducer. FIG. 11E shows a schematic view illustrating the directions of the ultrasonic waves emitted by the ultrasonic transducer employing convex transducing elements and the beam width BW formed by superposition of soundwaves. FIG. 11F shows a schematic view illustrating the directions of the ultrasonic waves emitted by the ultrasonic transducer employing a convex micro array of transducing elements and the beam width BW formed by superposition of soundwaves. FIG. 11G shows a schematic view of a zipper-grouped M-column-N-row (M×N) array of transducing elements (ZMN) with electronic focusing of the present invention, which substantially equivalently replaces focusing by folded structure and/or focusing by an acoustic lens.

As shown in FIG. 11A, such folded structure is formed by folding the surface 140 into a left sub-surface 140L and a right sub-surface 140R. The folding between any adjacent columns of transducing elements can adjust the elevation sound energy density curve ESEDC, the elevation focus EF, the beam width BW, and the elevation thickness ET. The left sub-surface 140L is not parallel to the right sub-surface 140R, and, in particular, the designed angle θ between the sub-surfaces can make the left ultrasonic longitudinal detection plane PL intersects or partially overlaps the right ultrasonic longitudinal detection plane PR (within a certain depth), and may decrease the thickness of the left ultrasonic longitudinal detection plane PL and the right ultrasonic longitudinal detection plane PR in the elevation axis X. It should be noted that, in FIGS. 11A to 11F, the left transducing elements 144L span the left sub-surface 140L and the right sub-surface 140R, and the right transducing elements 144R also span the right sub-surface 140R and the left sub-surface 140L, so that the left transducing elements 144L and the right transducing elements 144R may overlap each other on the elevation axis X, and form the folded zipper array of the present invention.

Although the folded structure in FIG. 11A can make the left ultrasonic longitudinal detection plane PL intersect or partially overlap the right ultrasonic longitudinal detection plane PR, an acoustic lens 16 may still be added to adjust the beam width BW and the mixing of the ultrasonic waves from both of left and right sides. In the example of FIG. 11B, the acoustic lens 16 is a multifocal lens (or progressive lens) with multiple focuses targeting the central plane C. If the transducer is designed to have a folded structure, it may use a thinner acoustic lens to reduce the energy loss of the ultrasonic wave. As shown in FIG. 11C, a multifocal lens can produce a stretched focal zone (instead of a focal point), which also makes the beam width BW thinner.

In FIG. 11D, the transducing elements may be arranged at different heights on the axial axis Z to form a convex surface or a concave surface, or a transducing element per se may be made convex or concave, in order to adjust the elevation focus (or axial focus), thereby reducing the thickness of the acoustic lens, or even omitting the acoustic lens, which can reduce the loss of the ultrasonic energy. The size of a transducing element in the micro array is much smaller than the size of a general transducing element. In FIG. 11D, the lines behind the transducing elements in the micro array represent the wires of the control circuit. A comparison may be made among FIGS. 11C, 11E, and 11F.

In FIGS. 11C to 11F, comparisons are made between the schematic views of the XY plane and the XZ plane, moreover, the transducing elements 144L, 144R are overlapped in the elevation axis and both extend across the midline to form a zipper structure. FIGS. 11A and 11B are simplified schematic views thereof.

FIG. 11G shows the XY plane and the XZ plane schematic views of a zipper-grouped M-column-N-row (M×N) micro array of transducing elements (ZMN) of the present invention, which can perform electronic focusing and substantially equivalently replaces focusing by a folded structure and/or an acoustic lens. Herein, the two-column-N-row (2×N) zipper array of right triangle transducing elements (Z2N) formulate the fundamental shape, and the array (Z2N) are further divided into a zipper-grouped M-column-N-row (M×N) micro array (ZMN). An electronic signal processing may be applied between any two arbitrary columns of transducing elements to increase or decrease time delay of its acoustic (or electric) wave, and to change phase differences and interference of acoustic (or electric) wave, and accordingly adjust the elevation sound energy density curve ESEDC, elevation focus EF, and/or elevation thickness ET, wherein the electronic signal processing can be implemented by a circuit, a chip, or a software.

In addition, the zipper-grouped M×N micro array of transducing elements (ZMN) may be a phase array, which forms an ultrasonic transducer with a fan-shape range to emit and receive the ultrasonic beam.

Figure 12A:
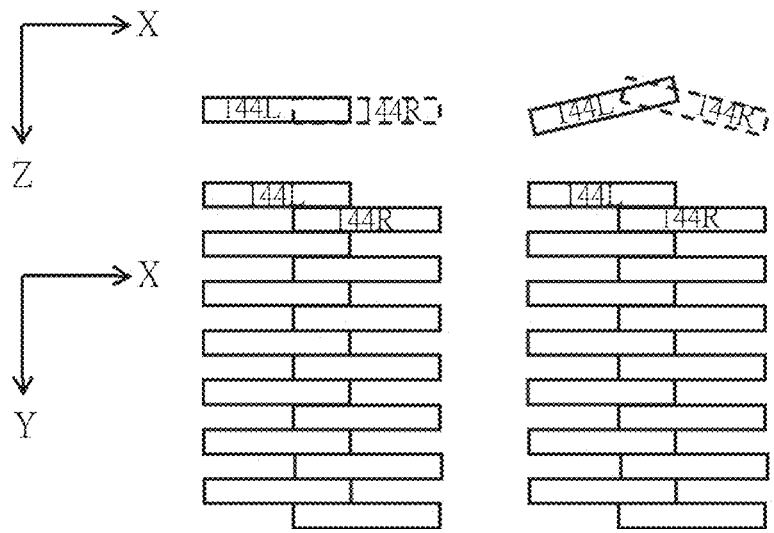
FIGS. 12A and 12B show the ultrasonic transducers with zipper arrays according to several embodiments of the present invention.
Figure 12B:
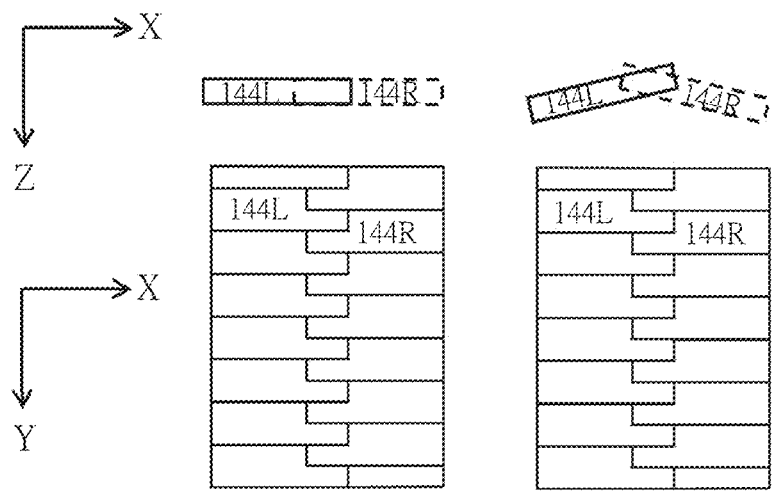

FIGS. 12A and 12B show more zipper arrays according to several embodiments of the present invention; wherein each figure schematically marks only one column of the left transducing elements 144L and only one column of the right transducing elements 144R. In FIGS. 12A and 12B, a non-folded zipper array is shown at left side, and a folded zipper array is shown at right side. The transducing elements in FIG. 12A are rectangle, and the transducing elements in FIG. 12B are L-shaped to minimize gaps or to form a tight arrangement. Moreover, in those XZ plane schematic views, to show the overlap in the elevation axis or the "zipper" arrangement, the solid lines represent left transducing element 144L and the dotted lines represent the right transducing element 144R. The examples of various shapes in the zipper array of the ultrasonic transducer in FIGS. 7A and 7B may be folded and tightly arranged with reference to FIGS. 12A and 12B.

Figure 13:
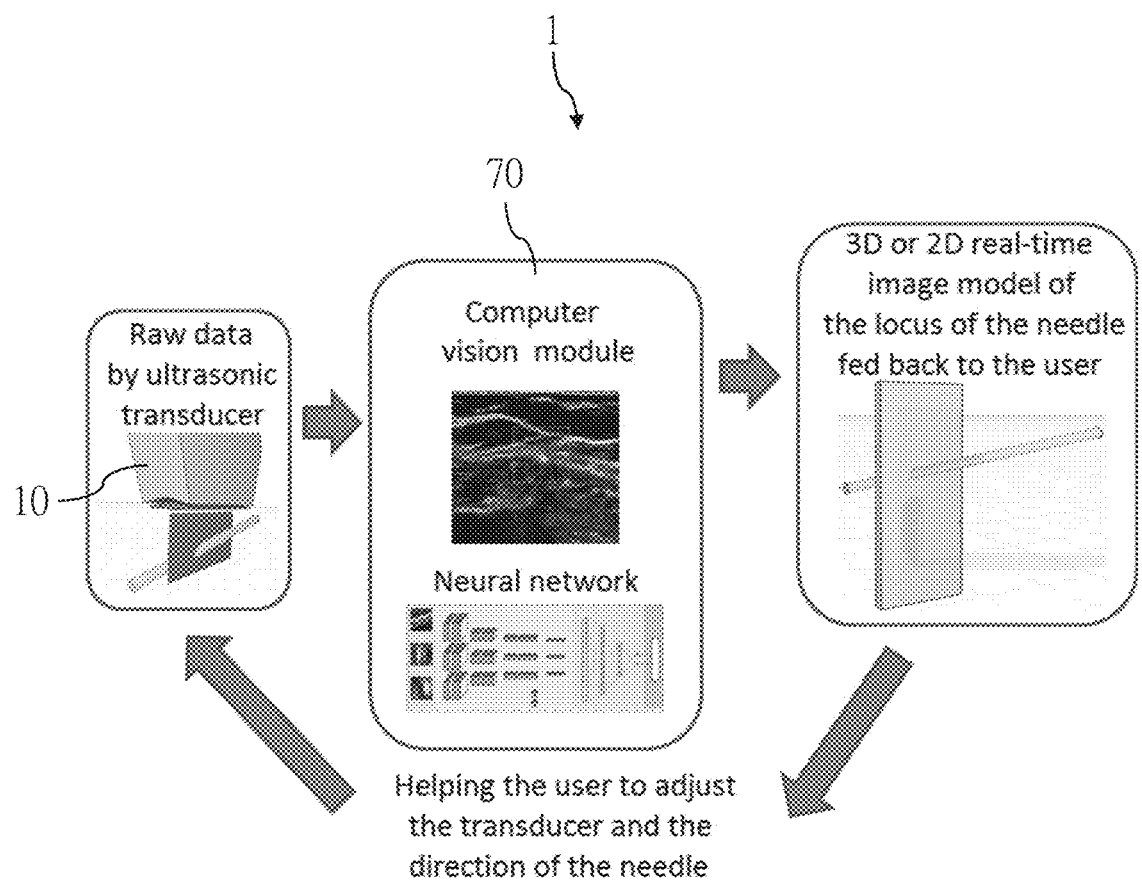
FIG. 13 shows a block diagram of the ultrasonic system according to one embodiment of the present invention.

FIG. 13 shows a block diagram of the ultrasonic system 1 according to one embodiment of the present invention. The ultrasonic transducer with a zipper array of transducing elements 10 of the present invention may be connected to a processing apparatus 70. The processing apparatus 70 can process the raw electronic signals from the ultrasonic transducer 10, in particular, the raw data of the needle image acquired from the left ultrasonic longitudinal detection plane PL and the right ultrasonic longitudinal detection plane PR. The processing apparatus 70 may have an artificial intelligence program such as a neural network, working with a computer vision software module, to process the acquired raw data of the needle image, in order to show the moving direction of the needle, as well as give an advice to the user about how to rotate the transducer to find the needle, or how to adjust the direction of the needle when reinserting the needle. Preferably, a three dimensional (3D) or two dimensional (2D) real-time image model may be display on a monitor, which can feedback the trajectory of the needle to the user, giving an assistance to the user to confirm the moving direction of the needle, wherein mirror moving directions of the needle can be ruled out. Besides, the processing apparatus 70 may also have a circuit, a chip, or a software that can connect the transducing elements in parallel, so as to realize the division, merge, delay of the signal from or to the transducing elements.

Figure 14:
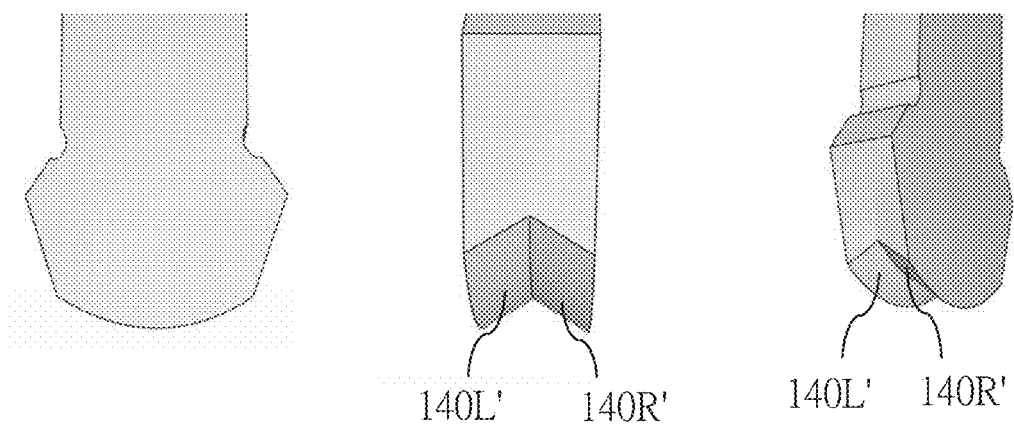
FIG. 14 shows a side view, a first perspective view, and a second perspective view of the ultrasonic transducer with a zipper array of transducing elements in a curved surface.

FIG. 14 shows a side view, a first perspective view, and a second perspective view of the ultrasonic transducer with a zipper array of transducing element in a curved surface.

In FIG. 14, the sub-surfaces 140R' and 140L' are curved surfaces in the direction of the lateral axis Y of the transducer. However, the only difference is the sub-surfaces being curved surfaces, the remaining components of the transducer in FIG. 14 can be referred to the relevant description in the other embodiments. (It should be specially noted that, the transducing elements in FIG. 11D can form a convex shape or concave shape, where the shapes are described in the direction of the elevation axis X of the transducer, while, the curved surfaces in FIG. 14 are described in the direction of the lateral axis Y of the transducer, these are two different concepts, but they can coexist in the same transducer.)

Although the present invention has been explained in relation to its preferred embodiment, it is to be understood that many other possible modifications and variations can be made without departing from the spirit and scope of the invention as hereinafter claimed.

What is claimed is:

1. An ultrasonic transducer (10) with a zipper array of transducing elements, comprising a tail (12) and a head (14); a surface (140) of the head (14) is embedded with two columns times N rows (2×N) of transducing elements, including N pieces of left transducing elements (144L) and N pieces of right transducing elements (144R); wherein the zipper array is defined in a way that each left transducing element (144L) is at least partially overlapped to each right transducing element (144R) in an elevation axis (X);

wherein each left transducing element (144L) comprises a left elevation focus projection line (LL) defined by projecting the apex position of a left elevation sound energy density curve (ESEDCL) on each left transducing element, and each right transducing element (144R) comprises a right elevation focus projection line (LR) defined by projecting the apex position of a right elevation sound energy density curve (ESEDCR) on each right transducing element;

wherein the left elevation sound energy density curve (ESEDCL) and the right elevation sound energy density curve (ESEDCR) are unequal and partially overlap with each other in the elevation axis, such that the left transducing element (144L) and the right transducing element (144R) have their respective elevation acoustic fields been partially overlapped or partially mixed, and accordingly form, by beamforming, a left ultrasonic longitudinal detection plane (PL) which is similar but not identical to a right ultrasonic longitudinal detection plane (PR); and wherein the left transducing elements (144L) and the right transducing elements (144R) work in emitting and receiving mechanisms as follows:

(i) using one side to emit the ultrasonic beam, and using the same side to receive the echo of the ultrasonic beam; or (ii) using one side to emit the ultrasonic beam, and using another side to receive the echo of the ultrasonic beam; or (iii) using one side to emit the ultrasonic beam, and using both two sides at the same time to receive the echo of the ultrasonic beam; or (iv) using both two sides at the same time to emit the ultrasonic beam, and also using both two sides at the same time to receive the echo of the ultrasonic beam to build a bilateral-equal-time-distance central ultrasonic longitudinal detection plane (PC) between the left ultrasonic longitudinal detection plane (PL) and the right ultrasonic longitudinal detection plane (PR); or (v) using both two sides at the same time to emit the ultrasonic beam, and using one side to receive the echo of the ultrasonic beam.

2. The ultrasonic transducer (10) of claim 1, wherein each left transducing element (144L) is interlocked with each right transducing element (144R) in terms of their shapes.

3. The ultrasonic transducer (10) of claim 1, wherein each left transducing element (144L) is complementary to each right transducing element (144R) in terms of their shapes to form a rectangle.

4. The ultrasonic transducer (10) of claim 1, wherein each left transducing element (144L) or each right transducing element (144R) is triangle, comb shape, trapezoid, wavy shape, or certain polygon shape other than rectangle.

5. The ultrasonic transducer (10) of claim 1, wherein a contact line (LD) exists between each left transducing element (144L) and each right transducing element (144R), and the contact line (LD) is a straight line, a polyline, or certain curve, such that the right transducing element is interlocked with the left transducing element to form any shape.

6. The ultrasonic transducer (10) of claim 1, wherein the left ultrasonic longitudinal detection plane (PL) is defined across the position having the suprathreshold ultrasonic beam energy emitted by the left transducing elements (144L) or the suprathreshold echo thereof received from the target object, or the suprathreshold part of the left elevation sound energy density curve (ESEDCL); the right ultrasonic longitudinal detection plane (PR) is defined across the position having the suprathreshold ultrasonic beam energy emitted by the right transducing elements (144R) or the suprathreshold echo thereof received from the target object, or the suprathreshold part of the right elevation sound energy density curve (ESEDCR), wherein the suprathreshold energy is arbitrary chosen to adjust the elevational dimension of the detection plane.

7. The ultrasonic transducer (10) of claim 1, wherein distance between the left ultrasonic longitudinal detection plane (PL) and the right ultrasonic longitudinal detection plane (PR) is determined by the distance between the left elevation sound energy density curve (ESEDCL)'s apex and the right elevation sound energy density curve (ESEDCR)'s apex, or determined by the distance between the left elevation focus projection line (LL) and the right elevation focus projection line (LR).

8. The ultrasonic transducer (10) of claim 1, wherein the ultrasonic transducer (10) is connected to a processing apparatus (70), configured to observe a trajectory of a needle or a needle-like instrument according to the left ultrasonic longitudinal detection plane (PL) and the right ultrasonic longitudinal detection plane (PR), and the processing apparatus is capable of distinguishing a mirror trajectory of a needle.

9. The ultrasonic transducer (10) of claim 8, wherein the processing apparatus is capable of building a bilateral-equal-time-distance central ultrasonic longitudinal detection plane (PC) between the left ultrasonic longitudinal detection plane (PL) and the right ultrasonic longitudinal detection plane (PR).

10. The ultrasonic transducer (10) of claim 1, wherein an acoustic lens (16) is attached in front of the left transducing elements (144L) and/or the right transducing elements (144R), and the acoustic lens (16) is configured to make the left ultrasonic longitudinal detection plane (PL) intersects or partially overlaps the right ultrasonic longitudinal detection plane (PR), and make the left ultrasonic longitudinal detection plane (PL) and the right ultrasonic longitudinal detection plane (PR) generate one or more elevation focuses (EFs).

11. The ultrasonic transducer (10) of claim 1, wherein the surface (140) has a left sub-surface (140L) and a right sub-surface (140R), wherein an angle $\theta$ is defined between the left sub-surface (140L) and the right sub-surface (140R).

12. The ultrasonic transducer (10) of claim 1, wherein the transducing elements in a basic zipper 2×N array (Z2N) are in the form of a zipper-grouped M×N micro array (ZMN), and a folded structure is formed between any adjacent columns of transducing elements so as to adjust the elevation sound energy density curve (ESEDC), the elevation focus (EF), and/or the elevation thickness (ET).

13. The ultrasonic transducer (10) of claim 1, wherein the transducing elements in a basic 2×N zipper array (Z2N) are in the form of a zipper-grouped M×N micro array (ZMN), wherein the zipper-grouping is achieved by certain electronic signal processing over electrodes of the transducing elements, so as to merge their electronic signals or cancel their divisions, such that the M×N micro array of transducing elements has its elevation sound energy density curve (ESEDC) substantially equivalent to that of the 2×N zipper array, wherein the electronic signal processing is achieved by a circuit, a chip, or a software.

14. The ultrasonic transducer (10) of claim 1, wherein the transducing elements in a basic 2×N zipper (Z2N) array are in the form of a zipper-grouped M×N micro array (ZMN), wherein certain electronic signal processing is applied between any two arbitrary columns of transducing elements to increase or decrease certain time delay of its acoustic or electric wave, so as to change phase difference and interference of the acoustic or electric wave, and accordingly adjust the elevation sound energy density curve (ESEDC), the elevation focus (EF), and/or elevation thickness (ET), wherein the electronic signal processing is implemented by a circuit, a chip, or a software.

15. The ultrasonic transducer (10) of claim 12, wherein certain electronic signal processing is applied between any two arbitrary columns of transducing elements in the zipper-grouped M×N micro array (ZMN) to increase or decrease time delay of its acoustic or electric wave, so as to change phase difference and interference of the acoustic or electric wave, and accordingly adjust the elevation sound energy density curve (ESEDC), the elevation focus, and/or elevation thickness, wherein the electronic processing is implemented by a circuit, a chip, or a software.

16. The ultrasonic transducer (10) of claim 13, wherein the zipper-grouped M×N micro array of the transducing elements (ZMN) is a phase array of an ultrasonic transducer, which has a fan-shape range to emit and receive the ultrasonic beam.

17. The ultrasonic transducer (10) of claim 1, wherein a portion of the surface (140) of the head (14) is a curved surface (140R', 140L') in the lateral axis Y to form a curved ultrasonic transducer with zipper array of the transducing elements.

\* \* \* \* \*